US006939705B1

(12) United States Patent
Schmidt et al.

(10) Patent No.: US 6,939,705 B1
(45) Date of Patent: Sep. 6, 2005

(54) METHOD OF PROTECTING L. JOHNSONII LA1 AGAINST STRESS

(75) Inventors: Gudrun Schmidt, Lausanne (CH); Ralf Zink, Le Mont Pélerin (CH)

(73) Assignee: Nestec S.A., Vevey (CH)

( * ) Notice: Subject to any disclaimer, the term of this patent is extended or adjusted under 35 U.S.C. 154(b) by 241 days.

(21) Appl. No.: 10/018,492

(22) PCT Filed: Jun. 9, 2000

(86) PCT No.: PCT/EP00/05403

§ 371 (c)(1),
(2), (4) Date: Mar. 6, 2002

(87) PCT Pub. No.: WO00/77186

PCT Pub. Date: Dec. 21, 2000

Related U.S. Application Data (60) Provisional application No. 60/138,946, filed on Jun. 11, 1999.

(51) Int. Cl.⁷ ............................ C12N 1/36; C12N 15/01
(52) U.S. Cl. .................. 435/245; 435/252.9; 435/244; 435/440
(58) Field of Search ............................ 435/252.9, 244; 435/245, 440

(56) References Cited

U.S. PATENT DOCUMENTS 5,962,062 A * 10/1999 Carrie et al. ................. 426/585

OTHER PUBLICATIONS

Broadbent et al., Systematic and Applied Microbiology, (1997) vol. 20, No. 1, pp. 12-19.*

Kilstrup et al., "Induction of Heat Shock Proteins DnaK, GroEL, and GroES by Salt Stress in *Lactococcus lactis*", *Applied and Environmental Microbiology*, May 1997, p. 1826-1837.

Flahaut et al., "Relationship Between Stress Response Towards Bile Salts, Acid and Heat Treatment in *Enterococcus faecalis*", *FEMS Microbiology Letters*, 138 (1996) 49-54.

Völker et al., "Stress Proteins and Cross-Protection by Heat Shock and Salt Stress in *Bacillus subtilis*", *Journal of General Microbiology*, (1992), 138, 2125-2135.

Gänzle et al., "Resistance of *Escherichia coli* and *Salmonella* Against Nisin and Curvacin A", *International Journal of Food Microbiology*, 48 (1999) 37-50.

Rocha et al., "Characterizatin of a Peroxide-Resistant Mutant of the Anaerobic Bacterium *Bacteroides frugilis*", *Journal of Bacteriology*, Nov. 1998, p. 5906-5912.

Grešíková et al., "Heat Shock Resistance in Filial Generation of Marine Vibrio S14", *Biologia*, Bratislava, 52/6: 717-722, 1997.

Davis et al., "Acid Tolerance in *Listeria monocytogenes*: The Adaptive Acid Tolerance Response (ATR) and Growth-Phase-Dependent Acid Resistance", *Microbiology*, (1996), 142, 2975-2982.

Smith et al., "Relationship of Water Activity to Prevention of Heat Injury in *Staphylococcus aureus*", *Lebensm.-Wiss. u.-Technol.*, 16, 195-197 (1983).

Kramer et al., "Oxidative Mechanisms of Toxicity of Low-Intensity Near-UV Light in *Salmonella typhimurium*", *Journal of Bacteriology*, May 1987, p. 2259-2266.

Schmidt et al., "Basic Features of the Stress Response in Three Species of Bifidobacteria: *B. Longum, B. adolescentis, and B. breve*", *International Journal of Food Microbiology*, 55 (2000) 41-45.

Elkins et al., "Protective Role of Catalase in *Pseudomonas aeruginosa* Biofilm Resistance to Hydrogen Peroxide", *Applied and Environmental Microbiology*, Oct. 1999, p. 4594-4600.

Lee et al., "HSP16.6 Is Involved in the Development of Thermotolerance and Thylakoid Stability in the Unicellular Cyanobacterium, *Synechocystis* sp. PCC 6803", *Current Microbiology*, vol. 40 (2000) pp. 283-287.

* cited by examiner

*Primary Examiner*—Irene Marx
(74) *Attorney, Agent, or Firm*—Bell, Boyd & Lloyd LLC (57) ABSTRACT

A bacterial cell having protection against conditions which are lethal to an unprotected bacterial cell wherein, the protected cell is obtained by subjecting a bacterial cell to treatment with a sublethal level of stress.

2 Claims, 9 Drawing Sheets

METHOD OF PROTECTING *L. JOHNSONII* LA1 AGAINST STRESS

This application claims benefit of provisional application 60/138,946 filed Jun. 11, 1999.

The present invention relates to a bacterial cell having protection against stress including the affects of extreme temperature change and osmotic shock; a nutritive or medicinal composition comprising the protected bacterial cell; and a method of protecting bacteria against stress.

Within the context of this specification the word "comprises" is taken to mean "includes, among other things". It is not intended to be construed as "consists of only". In addition, the word "stress" is used interchangeably with the term "adverse conditions". It includes, but is not limited to, adverse conditions of temperature (heat shock, cold shock), salt (osmotic shock), pH (pH shock), chemical stresses (antibiotics, alcohol, $H_2O_2$, etc.), nutritional stress, UV-stress, cold stress and oxygen concentration (oxidative stress).

Standard amino acid, RNA and DNA codes are used within this specification which are defined by the IUB Biochemical Nomenclature Commission.

It is well known that bacteria such as lactic acid bacteria (LAB) are ubiquitously found in the environment and they are largely used for the production of fermented products. For example, in the food industry bacteria are used in fermentation of milk products and production of starter cultures. During production of starter cultures, food fermentation, manufacture and storage, the bacteria that are employed must deal with different kinds of adverse conditions which generally have the effect of dramatically reducing their viability, stability and activity. These adverse conditions vary with production requirements and include thermal shock (freeze-drying or spray-drying), osmotic shock (drying) and pH shock (fermentation). It will be appreciated that the susceptibility or inability of bacteria to cope with these stresses is a problem in cases where bacteria are used on a large scale.

The presence of *Bifidobacteria* or *lactobacilli* in the human intestine, primarily the small and large intestine, is generally accepted as a contributing factor for a healthy well-being. In addition, it is considered that *Bifidobacteria* and *lactobacilli* may be useful in prophylaxis or treatment of ailments including gastrointestinal infections. In the light of this, it has been suggested that large populations of *Bifidobacteria* and *lactobacilli* in the intestine should be maintained and products comprising the bacteria should be administered. Often these products comprise different species of *Bifidobacteria* or *lactobacilli*. However, the stresses that *Bifidobacteria* and *lactobacilli* are exposed to during manufacture and storage of the products can significantly reduce their viability and/or physiological activity.

The natural response by bacterial cultures to sublethal temperature shifts or other sublethal stresses (including exposure to oxygen and osmotic shock) includes rapid expression of a distinct set of polypeptides called "stress-proteins". These proteins have been shown to enable Gram-positive bacteria such as for example *Lactococcus lactis, Bacillus subtilis, Lactobacillus acidophilus, Lactobacillus sakei, Enterococcus faecalis*, and *Lactobacillus johnsonii* to adapt to otherwise growth-limiting conditions.

One of the most studied stress proteins are the heat shock proteins or chaperones. These proteins are generally involved in the maturation of newly synthesised proteins, and they assist in refolding of denatured proteins. Numerous stress-response genes have been characterised in LAB, including those encoding the two major chaperone machines (groES/groEL and hrcA/grpE/dnaK/dnaJ) involved in the proper folding of newly synthesised proteins and the repair of those that are denatured.

Remarkably, it has now been found that bacteria, including *Bifidobacteria* and *lactobacilli*, can be protected against levels of stress that are lethal in unprotected bacteria. Surprisingly, this can be done by subjecting the bacteria to a sublethal level of stress treatment. It has surprisingly been found that after this initial stress treatment a higher level of stress is required to adversely affect the bacteria. This is unexpected because it was thought that cells which are damaged by stress would be less likely to cope with additional stress. In fact, the converse has been found—pre-stressed cells are able to bear a higher stress level compared to control cells which have not been pre-stressed.

Protection against one form of stress acquired by treatment with a dissimilar form of stress has been referred to as "cross-protection". This is unexpected because it was thought that cells damaged by treatment with one stress should render them more sensitive against an additional sublethal or lethal stress.

Accordingly, in a first aspect the invention provides a bacterial cell having protection against conditions which are lethal to an unprotected bacterial cell wherein, the protected cell is obtained by subjecting a bacterial cell to treatment with a sublethal level of stress.

In a second aspect, the invention provides a nutritive composition which comprises bacteria having protection against conditions which are lethal to unprotected bacteria wherein, the protected bacteria are obtained by subjecting bacteria to treatment with a sublethal level of stress and allowing them to recover.

In a further aspect, the invention provides a method of protecting a bacterial cell against stress which comprises the steps of treating a bacterial cell with a sublethal level of stress selected from the group which comprises thermal shock, osmotic shock, pH shock, oxidative stress, chemical stress, nutritional stress, V-stress, cold stress.

Preferably the method includes the additional step of allowing the cell to recover.

Preferably chemical stress is provided by treatment with antibiotics, alcohol or $H_2O_2$.

Preferably, the bacterial cell is selected from the group which comprises *Bifidobacteria*, lactic acid bacteria, *enterococci, streptomyces*, and *bacilli*.

More preferably, the bacterial cell is *Bifidobacterium longum, Bifidobacterium adolescentis, Bifidobacterium breve* or *Lactobacillus johnsonii*. An advantage provided by these bacteria is that they have the ability to rapidly acidify their substrate, therefore producing microbiologically safe products. In addition they contribute to a healthy well-being in humans and animals. Furthermore, they display a protective role against attack by enteric pathogens and are associated with anti-carcinogenic, anti-mutagenic and anti-tumorgenic activities. Without wishing to be bound by theory, recent reports suggest that they might act directly in the intestinal tract through antimicrobial activity, indirectly through immunomodulation via intestinal cells or by modifying the function of the normal indigenous microflora.

Preferably bacteria, more preferably *Bifidobacteria* and *lactobacilli*, are treated with sublethal salt concentrations to protect them against otherwise lethal salt concentrations or the cells are treated with sublethal thermal stress to protect them against otherwise lethal temperatures. Furthermore, results show that treatment with salt (e.g. NaCl) protect these bacteria against lethal thermal stress or against lethal cycles of freeze-thawing. Accordingly, the invention alternatively includes the steps of treating cells with salt to protect against thermal stress or treating the cells with adverse temperature conditions to protect against salt stress.

Preferably the bacterial cells are selected from *Bifidobacterium longum*, *Bifidobacterium adolescentis* or *Lactobacillus johnsonii*. More preferably the bacterial cells are selected from *Bifidobacterium longum* NCC481, *Bifidobacterium adolescentis* NCC251 or *Lactobacillus johnsonii* La1.

Preferably, protection against lethal salt concentrations (eg of between 0.1% and 0.4%) is carried out by treatment with about 0.01 to about 0.1% salt for about 15 to about 60 min. Preferably the salt is bile salt.

Preferably protection against lethal thermal stress (eg of between about 50° C. to about 60° C.) is carried out by treatment at about 37° C. to about 50° C. for about 15 to about 60 min or by treatment with a salt concentration of between about 1% and about 4% for about 30 to about 60 min.

Preferably, protection against freeze-thawing (eg 1 to 10 cycles) is carried out by treatment of the cells with salt concentration of between 1% and 4%.

Preferably *Bifidobacterium longum* NCC481 cells are protected. More preferably, protection of *Bifidobacterium longum* NCC481 cells is carried out in the logarithmic phase of their growth cycle against lethal bile salt concentrations (eg of between about 0.2% and about 0.3% for 30 min) by subjecting the cells to about 0.1% bile salt for about 30 min before lethal challenge.

Preferably, protection of *Bifidobacterium longum* NCC481 cells is carried out in the stationary phase of their growth cycle against lethal bile salt concentrations (eg of about 0.075% and about 0.15% for about 30 min) by treatment of the cells with about 0.05% bile salt for about 30 min before lethal challenge.

Preferably, *Bifidobacterium adolescentis* NCC251 cells are protected. More preferably, protection of *Bifidobacterium adolescentis* NCC251 cells is carried out in the logarithmic phase of their growth cycle against lethal bile salt concentrations (eg of between about 0.3% and about 0.4% for about 30 min) by subjecting the cells to about 0.1% bile salt for about 30 min before lethal challenge.

Preferably, protection of *Bifidobacterium adolescentis* NCC251 cells is carried out in the stationary phase of their growth cycle against a lethal bile salt concentration (eg of about 0.15% for about 30 min) by subjecting the cells to about 0.1% bile salt for about 30 min before lethal challenge.

Preferably, protection of *Bifldobacterium adolescentis* NCC251 cells is carried out in the stationary phase of their growth cycle against the otherwise lethal effect of (eg about 3 to about 4 cycles) freeze-thawing (about −80° C. to about room temperature (preferably about 20° C. to about 30° C., more preferably 25° C.)) by subjecting the cells to about 2% of NaCl for about 1 h.

Preferably, protection of *Bifidobacterium adolescentis* NCC251 cells is carried out in the logarithmic phase of their growth cycle against an otherwise lethal temperature of 55° C. for 20 min by treatment of the cells for about 30 min at about 45° C., about 15 min at about 47° C. or for about 1 h with 1% or 2% NaCl.

Preferably *Lactobacillus johnsonii* La1 cells are protected. More preferably, protection of *Lactobacillus johnsonii* La1 cells is carried out in the logarithmic phase of their growth cycle against an otherwise lethal temperature of 55° C. for up to 1 h by treatment of the cells with about 3.5% NaCl for about 15 min or about 48° C. for about 15 min.

Preferably, protection of *Lactobacillus johnsonii* La1 cells is carried out in the stationary phase of their growth cycle against an otherwise lethal temperature of 55° C. for up to 1 h by treatment of the cells with a temperature of about 48° C. for about 15 min or with about 3.5% NaCl for about 15 min.

Embodiments of the invention will now be described in further detail with reference to the accompanying drawings in which.

C. Afterwards the samples were shifted to 55° C. and the viable cell counts were determined after 30 min and 60 min.

STRAINS AND GROWTH CONDITIONS

*Bifidobacterium adolescentis* NCC251, *Bifidobacterium longum* NCC481, *Bifidobacterium longum* NCC490, *Bifidobacterium longum* NCC585, and *Bifidobacterium breve* NCC298 were cultivated in MRS medium supplemented with 0.5 g/l cysteine at 37° C. under anaerobic conditions (98% nitrogen and 2% hydrogen). *Lactococcus lactis* MG1363 was grown in MRS medium at 30° C. *Escherichia coli* TG1 (Amersham) was cultivated in Luria-Bertani medium at 37° C. *Lactobacillus johnsonii* La1 was grown in MRS at 37° C.

Stress Treatment

Cells were grown to an OD600 (optical density at 600 nm) between 0.4 and 0.7 or taken in the stationary phase and subjected for different times to various stress conditions. Cells used for freeze-thawing experiments were concentrated in saline solution before being subjected to −80° C. Salt stress was exerted by adding sodium chloride to the samples while for bile-salt stress OXGALL (Trade Mark) (Difco) was used.

The stress treatment of *Bifidobacteria* was performed under anaerobic conditions while the determination of viable cells was carried out under aerobic conditions. Cells of *lactobacilli* were grown under microaerophil conditions, stress treatments and determination of viable cell counts was performed under aerobic conditions.

*Bifidobacteria*

Ranges for inductions and lethal challenges

|  | pre-induction | lethal challenge |
| --- | --- | --- |
| pH (e.g. HCl): | pH 6.0–3.5 | pH 2.5–2 |
| Bile (e.g. Oxgall): | 0.01%–0.1% | 0.075%–0.4% |
| Temperature: | 37° C.–48° C. | 50° C.–60° C. |
| Salt (e.g. NaCl): | 0.5%–3% | 3%–8% |

Time of pre-induction and lethal challenge can vary dependent on strain and stress conditions between 5 min to 2 h.

*Lactobacilli*

Ranges for inductions and lethal challenges

|  | pre-induction | lethal challenge |
| --- | --- | --- |
| pH (e.g. HCl, lactic acid) | pH 6.0–4.5 | pH 4.0–2 |
| Temperature | 40° C.–50° C. | 50° C.–60° |
| Salt (e.g. NaCl) | 0.5%–3.5% | 4%–8% |

Time of pre-induction and lethal challenge can vary dependent on strain and stress conditions between 5 min to 2 h.

DNA Techniques

Isolation of chromosomal DNAs was carried out according to standard methods.

Analyses of mRNA

For Dot-blot hybridisation total RNA was isolated, denatured and transferred to uncharged nylon membranes (GeneScreen, NEN) according to standard methods. The membranes were pre-hybridised (1 h, 40° C.) and subsequently hybridised for 4h with 100 pmol DIG-labelled probes (Boehringer). The membranes were washed twice for 5 min in 2×SSC containing 0.1% SDS at 40° C. and once at the probe-dependent temperature, which was 46° C. and 48° C., respectively for the two dnaK specific probes GSR5 (5'-CATCGAAGGTGCCGCCAC-3') and GSR8 (5'-TCGT-CACCACCGAGGTG-3'), and 51° C. for the universal probe 1028R (5'-CCTTCTCCCGAAGTTACGG-3'). Detection was performed according to the manufacturers instructions.

PCR Amplification

The core dnaK region was amplified using the degenerate primers HS1 (5'-ATIACIGTICCIGCITA (T/C)TT(T/C)AA (TIC)GA-3') and HS2 (5'-CATIGT(T/C)TCIATICCIA(A/G) IGAIA(A/G)IGG-3') as well as 1 μg of chromosomal DNA as template. Amplification reactions were performed in a total volume of 100 μl (containing 200 μM each of dATP, dCTP, dGTP, and dTTP, 50 pmol of each primer, 2.5 U of Super-Taq DNA Polymerase (HT Biotechnology), and the corresponding 1×PCR buffer). Reactions were carried out with a Perkin-Elmer thermocycler: initial denaturation at 95° C. for 5 min followed by 30 cycles of 95° C. for 1 min, 55° C. for 1 min, and 72° C. for 1 min, with a final extension at 72° C. for 10 min.

Identification of the dnaK Gene

Based on the alignment of Barril et al. (1994), we chose two regions of the DnaK of *Lactococcus lactis, Escherichia coli* and *Bacillus megaterium* possessing identical amino acid sequences and designed two degenerate primers HS1 and HS2 corresponding to the amino acids at positions 114 to 122 and 366 to 374 of *Lactococcus lactis* DnaK, respectively. This primer pair was used for a PCR-amplification using chromosomal DNA of NCC481, NCC490, NCC585, NCC251, and NCC298 as templates. Two fragments were obtained for each strain. For all strains those fragments corresponding in size to that of the two positive controls *Escherichia coli* and *Lactococcus lactis* were isolated from an agarose gel, purified and sequenced. In each fragment an open reading frame was identified showing high sequence similarities to the core region of known DnaK proteins. Particularly high identities were observed to *streptomyces* and *mycobacteria* as well as to *Lactobacillus sakei, bacilli*, and *streptococci*.

mRNA Analysis of dnaK Gene Expression

Figure 1:
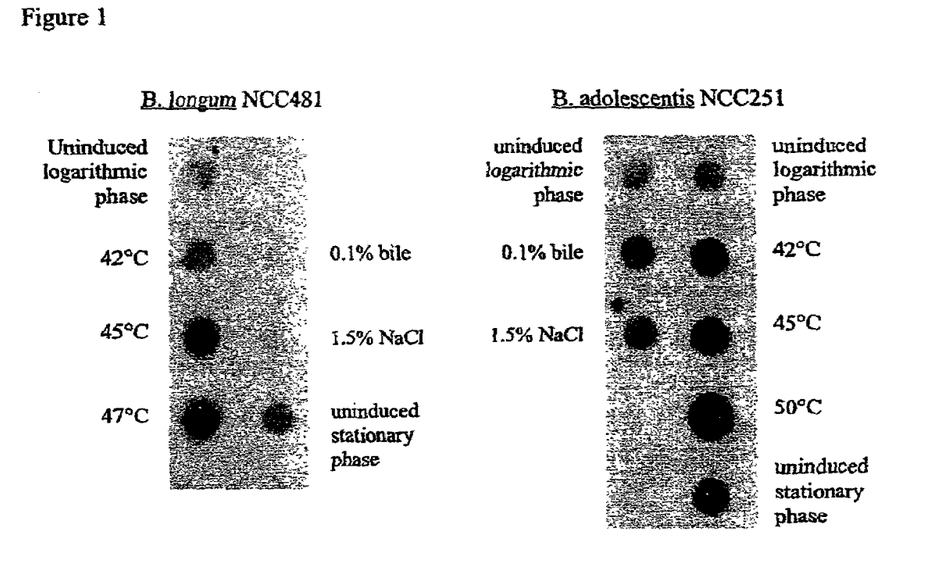
FIG. 1 shows results of a dot blot hybridization of RNA from cells of *Bifidobacterium longum* NCC481 and *Bifidobacterium* adolescentis NCC251 after 10 min exposure to different kinds of stress. Hybridization was performed using the specific probes GSR8 and GSR5 for NCC481 and NCC251, respectively.

The transcriptional induction of dnaK was investigated with cells exposed to heat shock and to additional general stress conditions. *Bifidobacterium longum* NCC481 and *Bifidobacterium adolescentis* NCC251 cells of the logarithmic phase were subjected to 0.1% bile salt, 1.5% NaCl or a heat shock for 10 min at 42° C. and 45° C. Maximum temperatures of 47° C. and 50° C. were tested for NCC481 and NCC251, respectively. Uninduced cells from the logarithmic and stationary phase were always used as controls. Total RNA was isolated and subjected to dot blot hybridization. The dnaK specific probes GSR8 and GSR5 were used for NCC481 and NCC251, respectively. The universal probe 1028R was chosen to verify the amount and quality of RNA on the membrane. An increased concentration of dnaK specific mRNA was observed when subjecting the cells to increasing temperatures (FIG. 1). In contrast to NCC251, dnaK of NCC481 was only slightly induced in cells entering the stationary phase. Furthermore a slight induction of dnaK was observed in NCC251 after bile-salt and NaCl treatment. No significant induction under identical conditions was obtained for NCC481.

Survival and Cross-Protection

Growth and survival of *Lactobacillus johnsonii* La1, *Bifidobacterium adolescentis* NCC251 and *Bifidobacterium longum* NCC481 at different temperature, bile-salts and salt conditions were tested.

Figure 2:
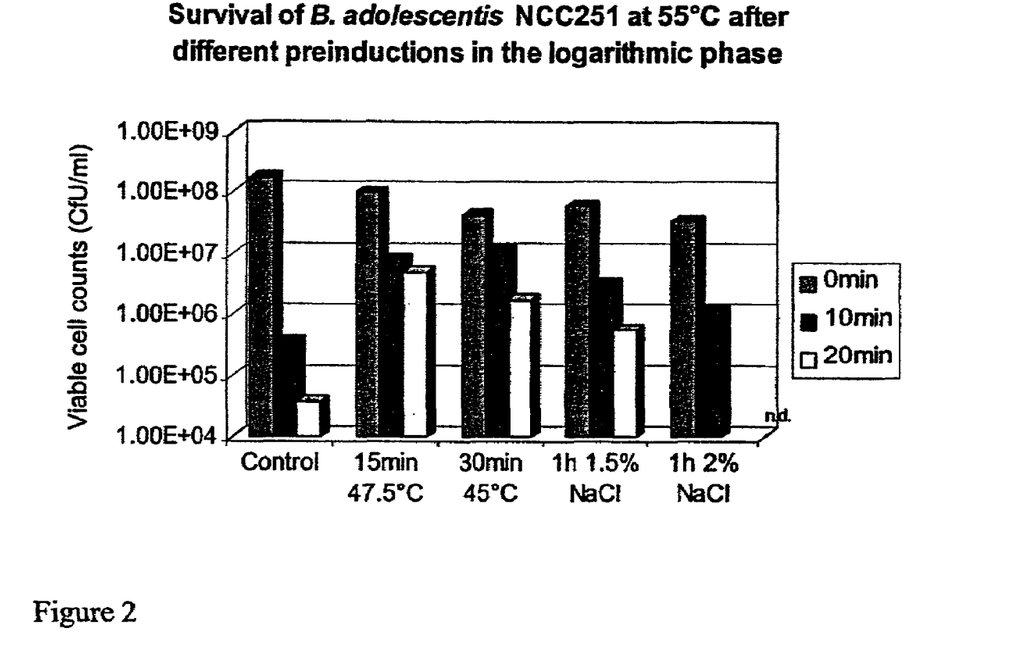
FIG. 2 shows a graph of survival of *Bifidobacterium adolescentis* NCC251 at 55° C. after different pre-inductions in the logarithmic phase. Cells were grown in MRS and cysteine at 37° C. to an OD600 of between 0.4 and 0.7. Aliquots were taken and subjected for 15 min to 47° C., for 30 min to 45° C., or 1 h to 1.5% NaCl or 2% NaCl; the control remained at 37° C. The samples were shifted to 55° C. and after 10 and 20 min the viable cell counts were determined.

Remarkably, logarithmic phase NCC251 showed an increased resistance to the generally lethal temperature of 55° C. after being treated with sublethal heat stress. An almost 24-fold and 128-fold higher thermotolerance was observed after subjecting the cells to 47° C. for 15 min prior to a heat shock for 10 min and 20 min, respectively (FIG. 2). These figures are remarkable because they show how that, unexpectedly effective pre-induction of cells can be to protect them against otherwise lethal challenges. A 9-fold and 15-fold cross-protection of cells against 55° C. was achieved by pretreatment for 1 h with 1.5% NaCl. An equal protection against thermal stress could also be observed by pre-inducing at 45° C. for 30 min or 2% NaCl for 1 h (FIG. 2).

Figure 8:
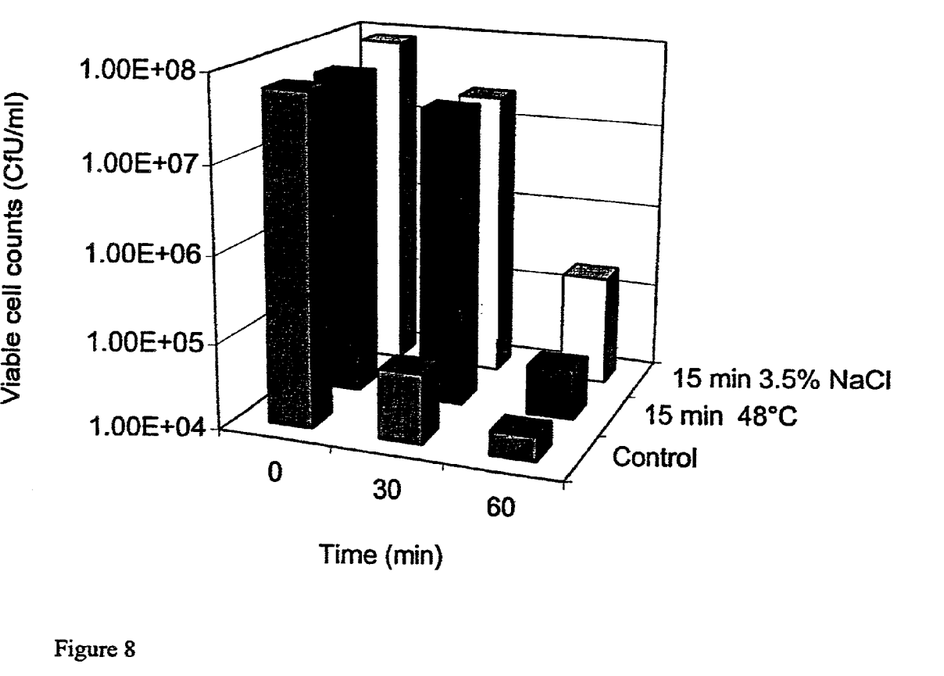
FIG. 8 shows a graph of survival of *Lactobacillus johnsonii* La1 under lethal thermal conditions. Cells were grown in MRS at 37° C. to an OD600 (optical density at 600 nm) between 0.4 and 0.7. Samples were taken and subjected to 3.5% NaCl or 48° C. for 15 min. The control remained at 37°

Cells in the logarithmic phase of the growth cycle of *Lactobacillus johnsonii* La1 showed a 400-fold higher protection against 55° C. for 30 min after being pretreated with 3.5% NaCl or 15 min 48° C. After one hour at 55° C., a 10-fold and 5-fold higher protection was observed against 55° C. in samples pretreated with 3.5% NaCl and 48° C. for 15 min, respectively (FIG. 8).

Figure 9:
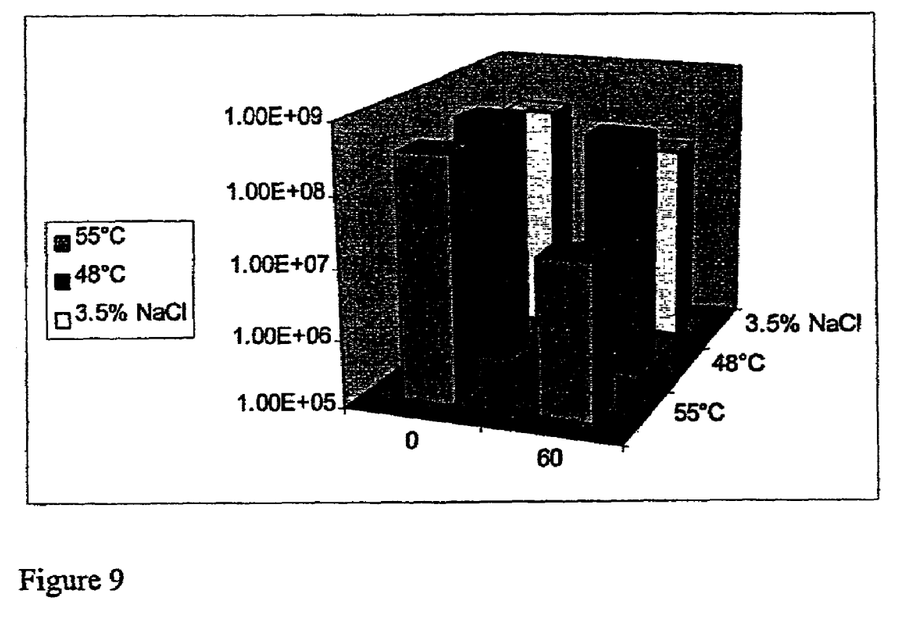
FIG. 9 shows a graph of survival of *Lactobacillus johnsonii* La1 in the stationary phase of their growth cycle under lethal thermal conditions. Samples were taken and subjected to 3.5% NaCl or 48° C. for 15 min. The control remained at 37° C. Afterwards the samples were shifted to 55° C. and the viable cell counts were determined after 60 min.

Stationary phase cells of *Lactobacillus johnsonii* La1 showed a remarkable 20-fold higher protection against 55° C. for 1 hour after being treated with 3.5% NaCl for 15 minutes at 48° C. (FIG. 9).

Figure 3:
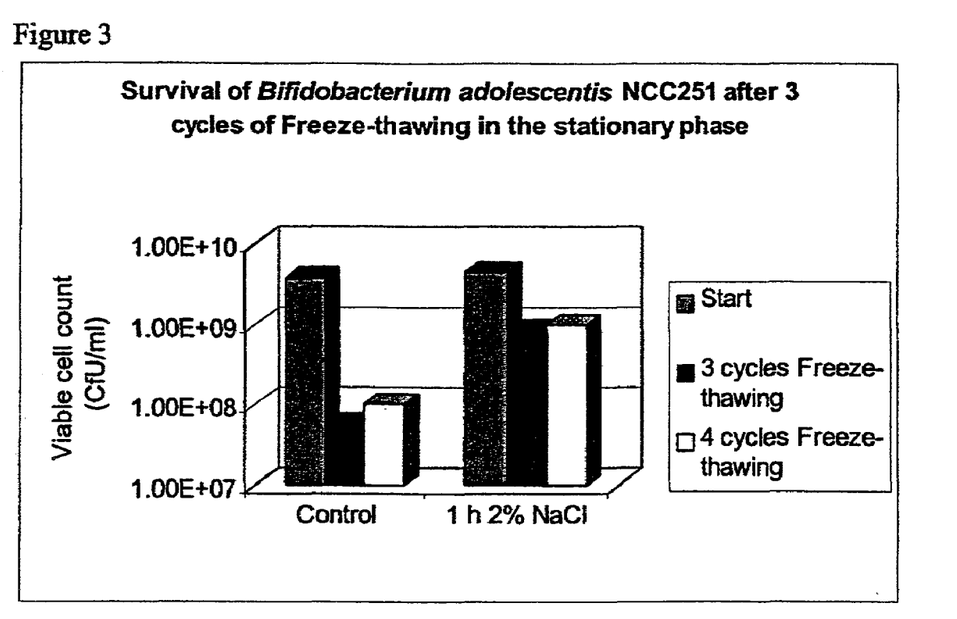
FIG. 3 shows a graph of survival of *Bifidobacterium adolescentis* NCC251 after three and four cycles of freeze-thawing. Stationary phase cells were taken and subjected for 1 h to 2% NaCl, the control remained without salt addition. The samples were shifted to −80° C. and thawed at room temperature. This cycle was repeated three and four times before the viable cell counts were determined.

Cells of *Bifidobacterium adolescentis* NCC251 in the stationary phase demonstrated a 14-fold higher survival after continuous cycles of freeze-hawing if pre-stressed with 2% NaCl for 1 h (FIG. 3). After 4 cycles of freeze thawing a 10-fold higher survival was observed.

Figure 4:
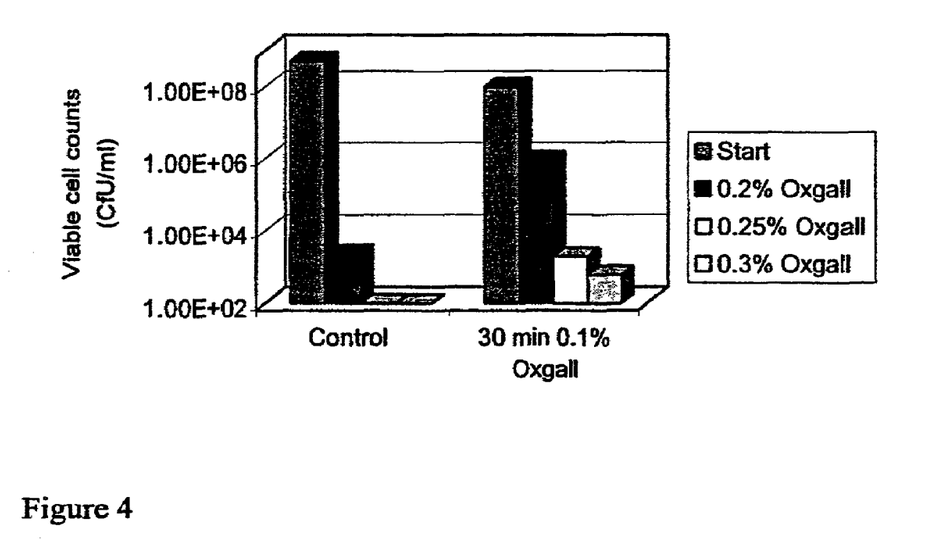
FIG. 4 shows a graph of survival of *Bifidobacterium longum* NCC481 under lethal bile salt conditions in the logarithmic phase. Cells were grown to an OD600 (optical density at 600 nm) between 0.4 and 0.7 and subjected for 30 min to 0.1% Oxgall. The control remained without Oxgall addition. The samples were aliquoted and shifted to 0.2%, 0.25%, and 0.3% Oxgall for 30 min, and the viable cell counts were determined.
Figure 5:
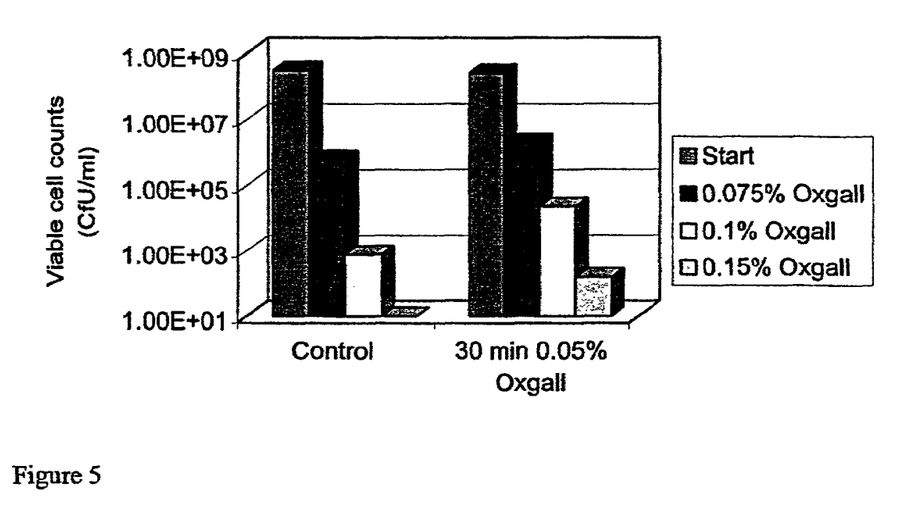
FIG. 5 shows a graph of survival of *Bifidobacterium longum* NCC481 under lethal bile salt conditions in the stationary phase. Cells were subjected for 30 min to an 0.05% Oxgall-treatment. The control remained without any Oxgall addition. The samples were aliquoted and shifted to 0.075%, 0.1%, and 0.15% Oxgall for 30 min, and the viable cell counts were determined.
Figure 6:
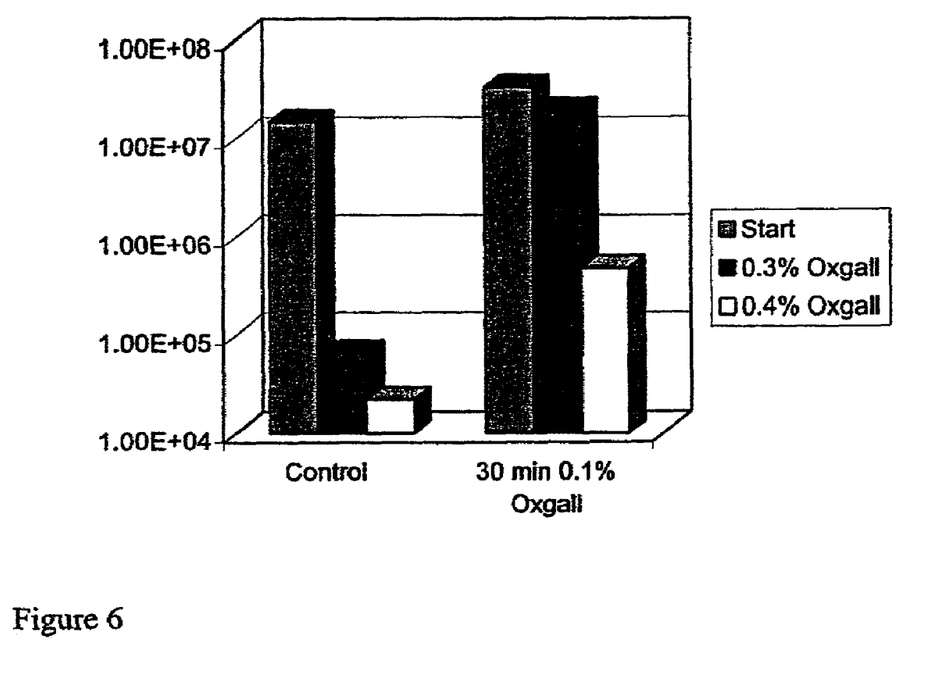
FIG. 6 shows a graph of survival of *Bifidobacterium adolescentis* NCC251 under lethal bile salt conditions in the logarithmic phase. Cells were grown to an OD600 (optical density at 600 nm) between 0.4 and 0.7 and subjected for 30 min to an 0.1% Oxgall-treatment. The control remained without any Oxgall addition. The samples were aliquoted and shifted to 0.3% and 0.4% Oxgall for 30 min, and the viable cell counts were determined.
Figure 7:
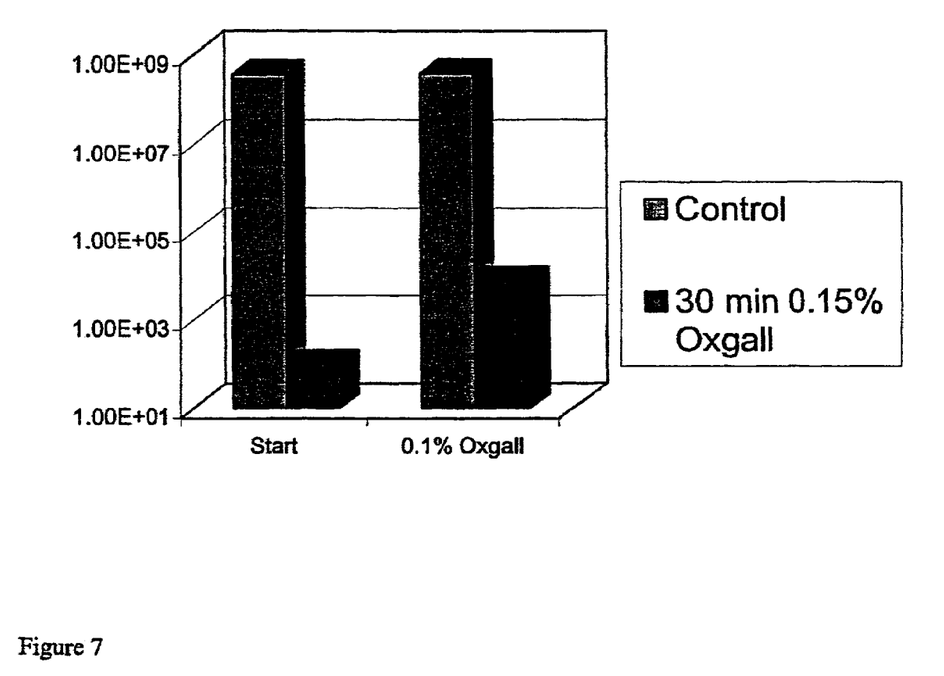
FIG. 7 shows a graph of survival of *Bifidobacterium adolescentis* NCC251 under lethal bile salt conditions in the stationary phase. Cells were subjected for 30 min to an 0.1% Oxgall-treatment. The control remained without any Oxgall addition. The samples were aliquoted and shifted to 0.15% Oxgall for 30 min, and the viable cell counts were determined.

Protection against lethal bile-salt concentrations could be observed in the logarithmic as well as in the stationary phase of *Bifidobacterium adolescentis* NCC251 and *Bifidobacterium longum* NCC481. A preconditioning (e.g. 30 min) of logarithmic cells with 0.1% bile-salts resulted in a 300-fold and 21-fold protection against 0.3% and 0.4% bile-salts in logarithmic phase cells of *Bifidobacterium adolescentis* NCC251, respectively, (FIG. 6). An 81-fold increased survival of stationary phase cells of *Bifidobacterium adolescentis* NCC251 (pre-induced with 0.1% bile-salts) was observed under the lethal concentration of 0.15% bile-salts (FIG. 7). Analogous results were obtained for *Bifidobacterium longum* NCC481. Logarithmic cells, pre-induced with 0.1% Oxgall showed a 400-fold, 1800-fold, and 580-fold better survival against the lethal concentrations of 0.2%, 0.25%, and 0.3% Oxgall, respectively (FIG. 4). Cells of the stationary phase showed a 3-fold, 29-fold, and 150-fold better survival for 30 min against 0.075%, 0.1%, and 0.15% Oxgall when they were pre-induced for 30 min with 0.05% Oxgall (FIG. 5).

In contrast to the results published by Flahaut et al. (1996) where a protection of *Enterococcus faecalis* cells against 0.3% bile salts could only be achieved for 30 seconds, remarkably cells were able to be protected for 30 min against lethal bile salt concentration. This could not have been predicted.

The core region of dnaK of *Bifidobacterium longum* NCC481, *Bifidobacterium longum* NCC490, *Bifidobacterium longum* NCC585, *Bifidobacterium adolescentis* NCC251, and *Bifidobacterium breve* NCC298 were PCR-amplified and identified. Subsequent mRNA analyses revealed that in NCC251 and NCC481 the induction of dnaK is regulated at the transcriptional level. Transcription is generally induced by heat and for NCC251 also by treatment with salt and bile-salts.

In the light of these findings it has been concluded that stress pre-treatment of *Bifidobacteria* and/or *lactobacilli* can lead to a significantly increased chances of survival under otherwise lethal homologous or heterologous stress conditions.

What is claimed is:

1. A method for protecting *Lactobacillus johnsonii* La1 against stress, which comprises the step of treating said *Lactobacillus johnsonii* La1 with about 3.5% NaCl for 5 minutes to 2 hours.

2. A method for protecting *Lactobacillus johnsonii* La1 against stress, which comprises the step of treating said *Lactobacillus johnsonii* La1 with a temperature of about 48° C. for 5 minutes to 2 hours.

* * * * *